US012611531B2

(12) United States Patent (10) Patent No.: US 12,611,531 B2
Gao et al. (45) Date of Patent: Apr. 28, 2026

(54) COATED MICRONEEDLE WITH MULTILAYER STRUCTURE, METHOD FOR PREPARING THE SAME AND MICRONEEDLE PATCH COMPRISING COATED MICRONEEDLE

(71) Applicant: TECHNICAL INSTITUTE OF PHYSICS AND CHEMISTRY OF THE CHINESE ACADEMY OF SCIENCES, Beijing (CN)

(72) Inventors: Yunhua Gao, Beijing (CN); Zequan Zhou, Beijing (CN); Suohui Zhang, Beijing (CN)

(73) Assignee: TECHNICAL INSTITUTE OF PHYSICS AND CHEMISTRY OF THE CHINESE ACADEMY OF SCIENCES, Beijing (CN)

( * ) Notice: Subject to any disclaimer, the term of this patent is extended or adjusted under 35 U.S.C. 154(b) by 573 days.

(21) Appl. No.: 18/024,585

(22) PCT Filed: Sep. 7, 2021

(86) PCT No.: PCT/CN2021/116904
§ 371 (c)(1),
(2) Date: Mar. 3, 2023

(87) PCT Pub. No.: WO2022/048682
PCT Pub. Date: Mar. 10, 2022

(65) Prior Publication Data
US 2023/0310822 A1 Oct. 5, 2023

(30) Foreign Application Priority Data
Sep. 7, 2020 (CN) .......................... 202010928436.2

(51) Int. Cl.
A61M 37/00 (2006.01)
A61K 9/70 (2006.01)
B05D 7/00 (2006.01)

(52) U.S. Cl.
CPC ....... *A61M 37/0015* (2013.01); *A61K 9/7023* (2013.01); *B05D 7/586* (2013.01);
(Continued)

(58) Field of Classification Search
CPC ...... A61M 37/0015; A61M 2037/0053; A61K 9/7023; B05D 7/586; B05D 2320/00
(Continued)

(56) References Cited

U.S. PATENT DOCUMENTS

2017/0196966 A1* 7/2017 Henderson ............... C12N 7/00

FOREIGN PATENT DOCUMENTS

CN 104921961 9/2015

OTHER PUBLICATIONS

International Search Report (English and Chinese) and Written Opinion of PCT/CN2021/116904 dated Nov. 29, 2021 11 pages.
(Continued)

*Primary Examiner* — Phillip A Gray
(74) *Attorney, Agent, or Firm* — Rankin, Hill & Clark LLP

(57) ABSTRACT

The present application discloses a coated microneedle with a multilayer structure, including a base, a needle tip on the base, and a functional coating. The functional coating includes a content including a water-soluble polymer material and an active ingredient, and a sustained-release layer wrapping the content. The sustained-release layer covers the needle tip. The coated microneedle can prevent a drug-containing matrix from being quickly dissolved and dispersed, prevent the active ingredient from exuding along with tissues at an action site, and increase the drug intake.
(Continued)

The present application further discloses a method for preparing the coated microneedle and a microneedle patch including the coated microneedle.

19 Claims, 5 Drawing Sheets

(52) U.S. Cl.
CPC . *A61M 2037/0053* (2013.01); *B05D 2320/00* (2013.01); *B05D 2520/00* (2013.01)
(58) Field of Classification Search
USPC .......................................................... 604/46
See application file for complete search history.

(56) References Cited

OTHER PUBLICATIONS

Zhou, et. al, Enhanced delivery efficiency and sustained release of biopharmaceuticals by complexation-based gel encapsulated coated microneedles: rhIFNa-lb example, Asian Journal of Pharmaceutical Sciences, 2021, pp. 612-622, 16, Beijing, China.

* cited by examiner

A                                    B 5X side pictures 4X stereomicroscope pictures

COATED MICRONEEDLE WITH MULTILAYER STRUCTURE, METHOD FOR PREPARING THE SAME AND MICRONEEDLE PATCH COMPRISING COATED MICRONEEDLE

TECHNICAL FIELD

The present application relates to the technical field of medicine, in particular to a coated microneedle with a multilayer structure and a method for preparing the same.

BACKGROUND

Transdermal administration is a common mode of administration. Compared with oral administration, it has a higher bioavailability and improves the compliance of patients with injection administration. With the development of microfabrication technology, the research process of microneedle administration has been quickly promoted. Microneedle is a kind of patch having a needle tip array with micron-level or millimeter-level height. When the microneedle acts on the skin, the needle tip is pressed into the skin to open the skin channel and increase the administration efficiency. At the same time, the microneedle manufacturing process is simple, the cost is low, the scope of applicable drugs is wide, the patient can administer the drug independently, and it has received widespread attention in recent years.

Microneedles can be divided into penetration promoting microneedles combined with drug-loaded patches or solutions, drug-loaded coated microneedles, hollow injection microneedles, drug-loaded dissoluble microneedles and drug-loaded or tissue fluid suction swelling microneedles. The development of microneedles aims at one or more specific drugs. It is necessary to investigate the influencing factors, accelerated stability, long-term stability, bioavailability, bioequivalence and other items of raw materials and preparations, so as to select a drug formula. The process is long and the cost is high. For the development of microneedles of most water-soluble drugs, especially polypeptide and protein drugs, in order to ensure the stability and bioavailability of active ingredients, the excipients in the prescription are mostly water-soluble polymer materials and sugars, which limit the development of this kind of drugs in the form of sustained-release microneedle preparations.

A series of articles such as Literature 1 (Drug Deli Transl Res. 2019 February; 9(1): 192-203.), Literature 2 (Drug Deliv Transl Res. 2016 October; 6(5): 486-97.), Literature 3 (Int J Pharm. 2015; 486(1-2): 52-8) respectively describe in detail the long-term stability prescription screening of poliovirus vaccine, influenza A vaccine virus and AsnB protein, the selection of the best buffer solution system, matrix excipients, surfactant and protective agent for protein drugs through a single-factor control variable, the influence of packaging temperature and humidity on drug activity and different formulas. The experimental period of the whole formula optimization is long, and the cost of raw materials and detection is high. The selected active substance formulas are all soluble quick-release microneedle preparations, which do not have a long-acting sustained-release function and still needs to be administered many times to achieve an effective immune response level.

Literature 4 (Eur J Pharm Biopharm. 2019 March; 136: 259-266.) and Literature 5 (J Control Release. 2012 Sep. 28; 162(3): 529-37) respectively describe the research on a dissoluble coated microneedle loading recombinant influenza virus hemagglutinin (HA) and an integrated dissoluble microneedle loading HIV-1 CN54gp140. The results of the immunological reactions produced by the drug-loaded microneedles and drug subcutaneous injection of the two show that the specific serum IgG and antibody titers produced by the microneedles used in BALB/c mice are slightly lower than those produced by the subcutaneous injection of the same dose, indicating that the quick-release coated microneedle and the integrated microneedle have the problems that the active ingredients are remained in the microneedle when they act on the living skin, and flow out with the tissue fluid when they penetrate the skin, which influence the utilization rate of the active ingredients.

SUMMARY

Based on the above facts, a first purpose of the present application is to provide a coated microneedle with a multilayer structure. The microneedle can prevent drug-containing matrix from being dissolved quickly, prevent active ingredients from seeping out with tissues ant an action site, and increase the drug intake. At the same time, it can also realize the substantiated release of a water-soluble microneedle active ingredient with a quick-release effect, can reduce the times of drug administration, and can improve the compliance of the patient.

A second purpose of the present application is to provide a method for preparing the coated microneedle according to the first purpose.

A third purpose of the present application is to provide a microneedle patch.

In order to achieve the first purpose, the present application adopts the following technical solution:

A coated microneedle with a multilayer structure, comprising a base, a needle tip on the base, and a functional coating, wherein the functional coating comprises a content comprising a water-soluble polymer material and an active ingredient, and a sustained-release layer wrapping the content; and the sustained-release layer covers the needle tip.

Further, the sustained-release layer is a delayed crosslinked sodium alginate system or a near-neutral chitosan system.

Further, raw materials of the delayed crosslinked sodium alginate system comprise a calcium source, a glucolactone and a carrier.

Further, the calcium source is one or more selected from the group consisting of sodium calcium edetate, calcium carbonate and calcium sulfate.

Further, the calcium source is sodium calcium edetate.

Further, the carrier is sodium alginate.

Further, the sustained-release layer is the delayed crosslinked sodium alginate system, and the sustained-release layer is a swelling structure formed through drying and crosslinking of mixed solution formed by mixing the raw materials comprising the calcium source, the glucolactone and the carrier in water.

Further, the viscosity of the mixed solution is 70 cps-13000 cps.

Further, the concentration of the calcium source in the mixed solution is 3 mmol/mL-0.3 mol/mL.

Further, the molar concentration of the glucolactone in the mixed solution is 1-2 times of the molar concentration of the calcium source.

Further, the sustained-release layer is the near-neutral chitosan system, and the sustained-release layer is a structure formed through drying and swelling of solution obtained by dissolving a chitosan material in an acidic solution and dialyzing to a near-neutral level in water. Preferably, the viscosity of the solution is 70 cps-13000 cps.

Further, the raw materials of the sustained-release layer further comprise a pore forming agent.

Further, the pore forming agent is one or more selected from the group consisting of sodium chloride, sodium carbonate, sodium bicarbonate, ammonium bicarbonate, polyvinylpyrrolidone, hyaluronic acid and sodium salt thereof, cellulose derivatives, trehalose, maltose and cyclodextrins.

Further, the pore forming agent accounts for 0.1-10 wt % of the total weight of the sustained-release layer.

Further, the water-soluble polymer material is one or more selected from the group consisting of carboxymethyl cellulose, hydroxypropyl methyl cellulose, hydroxyethyl cellulose, carboxymethyl chitosan, chitosan and derivatives thereof, polyvinyl alcohol and derivatives thereof, polyvinylpyrrolidone and derivatives thereof, sodium hyaluronate, chondroitin sulfate, dextran and derivatives thereof, sodium alginate, poly-gamma-glutamic acid, pullulan, gelatin, polydopamine and polyacrylamide.

Further, the active ingredient is one or more selected from the group consisting of water-soluble chemical drugs, polypeptide drugs, protein drugs and nucleic acid drugs.

Further, the active ingredient is one or more selected from the group consisting of water-soluble chemical drugs (such as leuprorelin, recombinant human insulin, thymopentin, recombinant human interferon, glutathione, terlipatide acetate, azelaic acid, gosserine, finasteride, aminofostine, tranexamic acid and metformin hydrochloride), polypeptide drugs, protein drugs or nucleic acid drugs.

Further, the solid content of the active ingredient does not exceed 2 times of the solid content of the water-soluble polymer material.

Further, a material for forming the base and/or needle tip comprises a biodegradable water-insoluble polymer material.

Further, the biodegradable water-insoluble polymer material is one or more selected from the group consisting of polyanhydrides, poly(orthoesters), polyphosphoesters, aliphatic polyesters and derivatives thereof.

Further, the polyanhydrides are one or more selected from the group consisting of P(CPP-SA), P(FA-SA) and P(FAD-SA).

Further, the aliphatic polyesters and derivatives thereof are one or more selected from the group consisting of polyglycolide, polylactide, glycolide-lactide copolymer, polycaprolactone, L-polylactic acid, racemic polylactic acid, polyethylene glycol-polylactic acid copolymer and derivatives thereof.

Further, the content further comprises a protective agent. Preferably, the protective agent is one or more selected from the group consisting of polyhydroxy compounds, carbohydrate compounds, serum albumin, polyvinylpyrrolidone, chondroitin sulfate, amino acids and surfactants.

Further, the protective agent accounts for equal to or less than 50%, preferably equal to or less than 10%, of the total mass of the content.

Further, the height of the functional coating is not more than ½ of the overall height of the needle tip, preferably not more than 3/7.

Further, the maximum diameter of the functional coating is not more than ⅔ of the bottom diameter of the needle tip, preferably not more than ½.

In order to achieve the second purpose, the present application adopts the following technical solution:

A method for preparing the coated microneedle with the multilayer structure, comprising:

providing a microneedle base comprising a base and a needle tip on the base;

applying aqueous solution of one part of a material for forming the sustained-release layer to the needle tip, and performing drying to obtain a swelling layer structure A covering the needle tip;

applying aqueous solution of a material for forming the content to a surface of the layer structure A, and performing drying to obtain the content on the surface of the layer structure A; and applying aqueous solution of the other part of the material for forming the sustained-release layer to the content to cover the content and combine with the layer structure A, and performing drying to obtain a swelling layer structure B, wherein the swelling layer structure A and the swelling layer structure B jointly form the sustained-release layer, and the content is wrapped in the sustained-release layer.

Further, a method for applying aqueous solution of a material for forming the content to a surface of the layer structure A is dipping; the number of times of dipping is preferably not less than 3, more preferably 3-10, most preferably 3-7.

Further, the range of the viscosity of the aqueous solution of the material for forming the content is 100 cps-12000 cps. For example, the range of the viscosity further comprises, but is not limited to, 200-10000 cps, 200-8000 cps, 200-5000 cps, 200-1000 cps, 200-500 cps, 400-10000 cps, 400-8000 cps, 400-1000 cps, etc.

In order to achieve the third purpose, the present application adopts the following technical solution:

A microneedle patch, comprising the coated microneedle with the multilayer structure according to any the first purpose, and a backing combined with the base of the coated microneedle.

The Present Application has the Following
Beneficial Effects

The coated microneedle provided in the present application realizes the sustained release effect of the water-soluble microneedle, is applicable to various existing water-soluble microneedle formulas, reduces the research and development cost of the sustained-release preparations, and is simple in preparation process and strong in operability. At the same time, the coated microneedle ensures a high utilization rate of drugs, can make the drugs release stably and slowly, extends the drug circulation time in the body, makes the blood drug concentration stable, and reduces the side effect of drug administration.

In the method for preparing the coated microneedle provided by the present application, the content is well wrapped in the sustained-release control layer to prevent the drugs from being released quickly in a short time. The method is simple in process and strong in operability, and is applicable to the change of the sustained-release preparations of a variety of quick-release water-soluble drug formulas. In addition, the change process does not require heating and irradiation. The used materials are non-toxic and have good biocompatibility. The stability and bioavailability of the original water-soluble microneedle preparation can be maintained to a large extent.

The microneedle patch provided by the present application also has the same effect as the coated microneedle because it contains the coated microneedle as described above. The microneedle patch has good skin puncture abil-
ity. The utilization rate of the loaded drugs is high. The
invasion is smaller than that of the injection preparation. It
is especially suitable for the development of microneedle
preparations of drugs having an obvious first-pass effect and
requiring frequent administration.

DESCRIPTION OF THE DRAWINGS

The specific examples of the present application will be
further described below in detail with reference to the
drawings.

DESCRIPTION OF THE EMBODIMENTS

Figure 1:
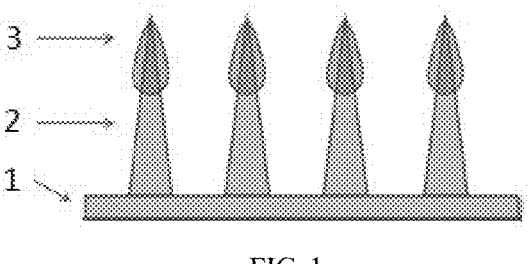
FIG. 1 illustrates a structural schematic diagram of a
coated microneedle in an example of the present application.

In order to describe the present application more clearly,
the present application will be further described below in
combination with the preferred examples with reference to
the drawings. Similar parts in the drawings are indicated by
the same reference signs. Those skilled in the art should
understand that the content described below is descriptive
rather than restrictive and should not limit the scope of
protection of the present application.

Figure 2:
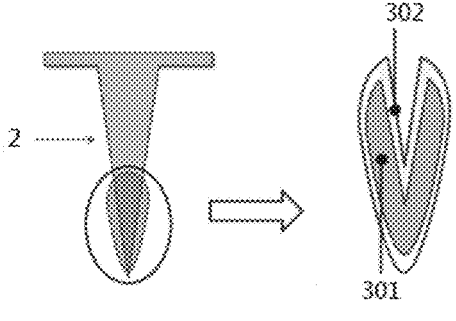
FIG. 2 illustrates a structural schematic diagram of a
functional coating in a coated microneedle in an example of
the present application.

According to a specific example of the present applica-
tion, provided is a coated microneedle with a multilayer
structure. Referring to FIG. 1 and FIG. 2, the coated
microneedle comprises a base 1, a needle tip 2 on the base
1, and a functional coating 3.

The functional coating 3 comprises a content 301 com-
prising a water-soluble polymer material and an active
ingredient, and a sustained-release layer 302 wrapping the
content 301.

The sustained-release layer 302 covers the needle tip 2.

In the coated microneedle, the existence of the sustained-
release layer 302 realizes the sustained release effect of the
dissoluble content 301, and can achieve the effect of delayed
release of drugs. When the microneedle acts on the skin, it
prevents the drug-containing matrix in the content 301 from
being dissolved quickly, prevents the active ingredient from
seeping out with the tissue at the action site, and increases
the drug intake. At the same time, it also has the effect of
slowly releasing the drug, and can reduce the number of
times of drug administration and improve the compliance of
the patient during administration to the patent.

In other words, in this example, the sustained-release
layer 302 can slowly release the dissoluble content without
reducing the total release of the content 301. At the same
time, the sustained-release layer is also required to have
good skin affinity to prevent skin allergy and better combi-
nation performance with needle tip materials. In a preferred
example, the sustained-release layer 302 is a crosslinked
layer structure. Specifically, it can be a swelling layer
structure. An exemplary raw material for forming the sus-
tained-release layer 302 includes a delayed crosslinked
sodium alginate system or near-neutral chitosan. The raw
material of the exemplary delayed crosslinked sodium alg-
inate system includes a calcium source, a glucolactone
(GDL) and a carrier. The carrier is preferably sodium
alginate. Optionally, the calcium source is one or more
selected from the group consisting of sodium calcium ede-
tate, calcium carbonate and calcium sulfate, and is prefer-
ably sodium calcium edetate.

Specifically, in case of a delayed crosslinked sodium
alginate system, a swelling structure obtained through dry-
ing and crosslinking of mixed solution formed by mixing the
calcium source, the glucolactone and the carrier in water is
the sustained-release layer 302. Preferably, the sustained-
release layer 302 is obtained through drying and crosslink-
ing by mixing the mixed solution of the calcium source and
the glucolactone with the aqueous solution of the carrier.

In the above example, the calcium source, as the calcium
source for calcium ion crosslinking, is a chelating state and
has no free calcium ion, which will not lead to crosslinking
the carrier such as sodium alginate. The glucolactone will be
slowly decomposed when it comes into contact with water,
to generate EDTA and gradually release $H^+$ ions. The $H^+$
ions and $Ca^{2+}$ compete for the chelating site on EDTA. A
part of EDTA Ca Na$_2$ forms EDTA Na$_2$H$_2$ and releases $Ca^{2+}$,
and forms crosslinking with the carrier such as sodium
alginate, for example. The decomposition of the glucolac-
tone in water is slow, so the release of $Ca^{2+}$ is also slow.
Therefore, it is recommended that all raw materials be added
quickly in a short time when the sustained-release layer
needs to be prepared, to prevent the premature change of
state to form gel that cannot be well coated onto the needle
tip.

The calcium source, the glucolactone and the carrier
sodium alginate are dissolved in water to form mixed
solution. The viscosity of the mixed solution is preferably 70
cps-13000 cps, so as to ensure that the coating and loading
of the microneedle tip sustained-release layer of the
microneedle are not influenced by the capillary phenomenon
of the low-viscosity solution, prevent the base of the
microneedle from being polluted, and simultaneously ensure
that the solution of the sustained-release layer has certain fluidity and can easily stay at the needle tip of the microneedle. In another preferred example, the concentration of the mixture of the calcium source and glucolactone in the mixture solution may be determined according to the required degree of crosslinking. The concentration of the calcium source in the mixture solution is preferably 3 mmol/mL-0.3 mol/mL. Preferably, the molar concentration of the glucolactone is 1-2 times of the molar concentration of the calcium source.

For example, the viscosity of the above mixed solution comprises, but is not limited to, 300-6000 cps, 300-5800 cps, 300-5700 cps, 320-6000 cps, 320-5800 cps, 320-5700 cps, 340-6000 cps, 340-5800 cps, 340-5700 cps, 300-500 cps, 340-3900 cps, 410-3850 cps, 410-5850 cps, 3050-5800 cps, etc.

Specifically, the near-neutral chitosan is prepared in acidic chitosan which is dialyzed to a near-neutral level in water. A swelling structure obtained after drying the solution is the sustained-release layer 302.

In the above example, chitosan is an electronegative polymer material, which is only soluble in acidic solution. The acidic solution may be composed of lactic acid, hydrochloric acid or acetic acid. Chitosan is dissolved in the acidic solution. The chitosan solution is acidic as a whole. The solution is dialyzed with ultrapure water to a near-neutral level, and then concentrated to a certain concentration. The solution will not be dissolved into normal saline/human tissue fluid after drying, and can be used for preparing a sustained-release layer.

The viscosity of the near-neutral chitosan solution is preferably 70 cps-13000 cps, so as to ensure that the coating and loading of the microneedle tip sustained-release layer of the microneedle is not influenced by the capillary phenomenon of the low-viscosity solution, and to ensure that the solution of the sustained-release layer has certain fluidity.

In this example, in the sustained-release layer 302 covering the content 301, it can be selected to add the pore forming agent according to the actual need. The pore forming agent helps intradermal water molecules to enter the content 301 inside the sustained-release layer 302 to regulate the drug release rate. Examples of the pore forming agent include, but are not limited to, one or more of sodium chloride, sodium carbonate, sodium bicarbonate, ammonium bicarbonate, polyvinylpyrrolidone, hyaluronic acid and sodium salt thereof, cellulose derivatives, trehalose, maltose and cyclodextrins. The actual amount of the pore forming agent may be preferably 0.1-10 wt % of the total weight of the sustained-release layer.

In another preferred example, the height of the functional coating 3 is not more than ½ of the overall height of the needle tip 2, preferably not more than ⅗; The maximum diameter of the functional coating 3 is not more than ⅔ of the diameter of the bottom of the needle tip 2, preferably not more than ½. This solution can make the microneedle maintain a good needle tip shape and have sufficient skin puncture ability. When puncturing the skin, the functional coating is not easily squeezed out by the skin, thus improving the amount of the functional coating entering the skin and improving the utilization rate of the drug.

In addition, in this example, the content 301 in the coated microneedle may be a conventional existing microneedle formula containing an active substance, thus greatly reducing the development cost of the sustained-release microneedle preparation of the drug. In the content, an exemplary water-soluble polymer material includes, but is not limited to, one or more selected from the group consisting of carboxymethyl cellulose, hydroxypropyl methyl cellulose, hydroxyethyl cellulose, carboxymethyl chitosan, chitosan and derivatives thereof, polyvinyl alcohol and derivatives thereof, polyvinylpyrrolidone and derivatives thereof, sodium hyaluronate, chondroitin sulfate, dextran and derivatives thereof, sodium alginate, poly-gamma-glutamic acid, pullulan, gelatin, polydopamine and polyacrylamide.

In another preferred example, the active ingredient refers to a substance used for diagnosis, treatment, prevention, cosmetics or health care purposes that is transmitted through the skin through the microneedle or microneedle patch in the present application and has the effect on animals or human bodies. According to this example, the active ingredient includes, but is not limited to, a pharmaceutical active ingredient, a vaccine active ingredient, a cosmetics active ingredient, a health care products active ingredient, etc., which may be selected according to the actual need. The amount of the active ingredient may be determined according to the solubility and stability of the specific active ingredient. Preferably, the solid content (i.e., mass) of the active ingredient does not exceed 2 times of the solid content of the water-soluble polymer material.

In the content, whether to add an assistant such as a protective agent may be determined according to the actual situation. Examples of the protective agent include, but are not limited to, one or more selected from the group consisting of polyhydroxy compounds, carbohydrate compounds, serum albumin, polyvinylpyrrolidone, chondroitin sulfate, amino acids, and surfactants. Preferably, the protective agent accounts for equal to or less than 10% of the total mass of the content.

In the coated microneedle, the base 1 and the needle tip 2 on the base 1 may be formed integrally or formed layer by layer. Materials for forming the base 1 and the needle tip 2 may be the same or different. In a preferred example, the material forming the base 1 and/or the needle tip 2 includes a biodegradable water-insoluble polymer material. An exemplary biodegradable water-insoluble polymer material includes, but is not limited to, one or more selected from the group consisting of polyanhydrides, poly(orthoesters) (POEs), polyphosphoesters (PPEs), aliphatic polyesters and derivatives thereof. Further, exemplary polyanhydrides include, but are not limited to, one or more of P(CPP-SA), P(FA-SA), and P(FAD-SA). Exemplary aliphatic polyesters and derivatives thereof include, but are not limited to, one or more selected from the group consisting of polyglycolide (PGA, also known as polyhydroxyacetic acid or polyglycolic acid), polylactide (PLA, also known as polylactic acid or polyhydroxypropionic acid), glycolide-lactide copolymer (PLGA or polylactic acid-glycolic acid copolymer), polycaprolactone (PCL), L-polylactic acid (L-PLA), racemic polylactic acid, polyethylene glycol-polylactic acid copolymer and derivatives thereof.

In a preferred example, the needle tip 2 is conical or polygonal; preferably, the needle tip 2 is conical, the needle spacing is less than or equal to 0.5 mm; the height is 0.2-0.7 mm.

Another example of the present application provides a method for preparing the coated microneedle with the multilayer structure. The method includes:

providing a microneedle base including a base 1 and a needle tip 2 on the base 1;

applying aqueous solution of one part of a material for forming the sustained-release layer 302 to the needle tip 2, and performing drying to obtain a swelling layer structure A covering the needle tip 2;

applying aqueous solution of a material for forming the
content 301 to a surface of the layer structure A, and
performing drying to obtain the content 301 on the
surface of the layer structure A; and applying aqueous solution of the other part of the material
for forming the sustained-release layer 302 to the
content 301 to cover the content 301 and combine with
the layer structure A, and performing drying to obtain
a swelling layer structure B, wherein the swelling layer structure A and the swelling layer
structure B jointly form the sustained-release layer 302,
and the content 301 is wrapped in the sustained-release
layer 302.

In the above methods, the method of applying is not
specifically limited, as long as the required combination can
be achieved. For example, it may be dipping. In addition, the
number of times of applying may be selected according to
the actual situation, which may be one or more. Preferably,
a method for applying the water solution of the material for
forming the content to the surface of the layer structure A is
dipping; the number of times of dipping is preferably equal
to or more than 3, more preferably 3-10.

In order to ensure that the coating and loading of the
microneedle tip sustained-release layer of the microneedle is
not influenced by the capillary phenomenon of the low-
viscosity solution, prevent the base of the microneedle from
being polluted, and ensure that the solution of the cross-
linked sustained-release layer has certain fluidity and can
easily stay at the needle tip of the microneedle to form a
crosslinked swelling sustained-release coating, the viscosity
of the aqueous solution of the material for forming the
sustained-release layer 302 is preferably between 70 cps and
13000 cps. Exemplarily, the viscosity of the aqueous solu-
tion includes, but is not limited to, 300-6000 cps, 300-5800
cps, 300-5700 cps, 320-6000 cps, 320-5800 cps, 320-5700
cps, 340-6000 cps, 340-5800 cps, 340-5700 cps, 300-500
cps, 340-3900 cps, 410-3850 cps, 410-5850 cps, 3050-5800
cps, etc.

In order to ensure that the content 301 can be well located
on the surface of the layer structure A, the apparent viscosity
of the aqueous solution of the material for forming the
content 301 is preferably 100 cps-12000 cps. Exemplarily,
the apparent viscosity of the solution of the material for
forming the content 301 includes, but is not limited to,
200-7000 cps, 250-7000 cps, 250-6500 cps, 250-600 cps,
250-1320 cps, 1000-6500 cps, 300-600 cps, etc.

In a preferred example, a method for providing a
microneedle base including a base 1 and a needle tip 2 on the
base 1 includes using a mold, placing a base 1 and/or needle
tip 2 material in the corresponding mold, performing heating
at temperature of 50-250° C. for 5-30 min, pressing the
material flat, and performing cooling and demolding to
obtain the corresponding base 1 and/or needle tip 2 material.
In a case that the microneedle base is integrated, an integral
mold is directly used; in a case that the microneedle base is
split, the base and the needle tip are then combined.

Another specific example of the present application pro-
vides a microneedle patch, which includes the coated
microneedle with the multilayer structure described above,
and a backing combined with the coated microneedle base 1.

The backing includes, but is not limited to, one of a
pressure-sensitive rubber backing, a hydrocolloid backing
and a silica gel backing.

A method for preparing the microneedle patch includes
preparing a microneedle array based on the preparation of
the coated microneedle and then bonding the backing on the
back side of the base.

The microneedle patch provided by the present applica-
tion can be applied to the fields of disease treatment,
prevention, health care and beautification.

The technical solutions of the present application will be
described below in combination with some specific
examples.

Example 1

Preparation of Multilayer Microneedle Including Sodium
Alginate Sustained-Release Layer Containing Bovine
Serum Albumin (BSA)

1) An appropriate amount of L-polylactic acid was placed
on an integrated microneedle matrix mold (that is, a
base and a needle tip were integrated). Vacuum pump-
ing was performed at a lower position of the mold. The
mold was heated at high temperature. The heating
temperature was 190° C. The heating time was 5 min.
A polymer material was pressed flat. Cooling and
demolding were performed to obtain an integrated
polylactic acid microneedle base (needle tip height was
700 μm and needle spacing was 500 μm).

2) By using water as a solvent, aqueous solution of
sodium alginate with a solid content of 2% was pre-
pared. Trehalose with a solid content of 0.5% was
added as a pore forming agent. By using water as a
solvent, 0.3 mol/L delayed crosslinking solution was
prepared, which was composed of 0.3 mol/L sodium
calcium edetate and 0.3 mol/L glucolactone. The aque-
ous solution of sodium alginate containing the pore
forming agent and the delayed crosslinking solution
were mixed according to the volume ratio v:v=10:1 to
prepare solution of a crosslinked swelling material with
a viscosity of 3700 cps. Uniform vortex mixing was
performed for 30 s at 4000 rpm. Concentration was
performed for 1 min at 5000 rpm. The solution was
stood for future use.

3) The prepared solution of the crosslinked swelling
material was placed in a drug loading tank with a height
of 300 μm. A piece of integrated polylactic acid
microneedle base was taken. The needle tip was down-
wards dropped into the drug loading tank for dipping.
Then, the microneedle was stood for 3 min to dry the
coating.

4) By using water as a solvent and polyvinyl alcohol (33.4
cps) as a matrix, heating and swelling were performed
to prepare 10% aqueous solution. 2% of trehalose was
added as a protective agent to prepare water-soluble
coating material solution. BSA was prepared into 16
mg/mL aqueous solution, which was mixed with the
above coating material solution according to volume
ratio v:v=1:1. Finally, drug solution containing 5% of
polyvinyl alcohol, 1% of trehalose and 6 mg/mL BSA
(i.e., content solution, the same as below) was formed.
The viscosity of the drug solution was 512 cps. Uni-
form vortex mixing was performed for 5 min at 2000
rpm. Centrifugation was performed for 1 min at 5000
rpm. The solution was stood for future use.

5) The prepared drug solution was placed in a drug
loading tank with a height of 300 μm. The microneedle
that had been loaded with the crosslinked swelling
coating was taken. The needle tip was downwards
dropped into the drug loading tank to dip the drug
solution. Then, the microneedle was stood for 3 min to
dry the coating. The solution dipping and drying pro-
cess was repeated 4 times.

6) The microneedle loaded with the crosslinked swelling coating and the drug-loaded coating was dipped in the crosslinked swelling material solution again. The microneedle was stood for 3 min to dry the coating to make the exterior of the drug-loaded coating of the coated microneedle be coated with the crosslinked swelling coating to obtain a coated microneedle wrapped by the swelling coating and loading BSA on the needle tip.

Figure 3:
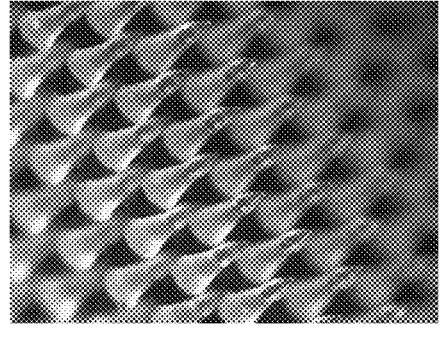
FIG. 3 illustrates a stereomicroscope picture of a BSA-
loaded coated microneedle prepared in example 1 of the
present application.
Figure 4:
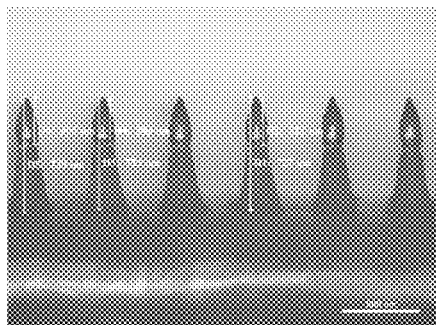
FIG. 4 illustrates a side picture of a BSA-loaded coated
microneedle prepared in example 1 of the present applica-
tion under a microscope.
Figure 5:
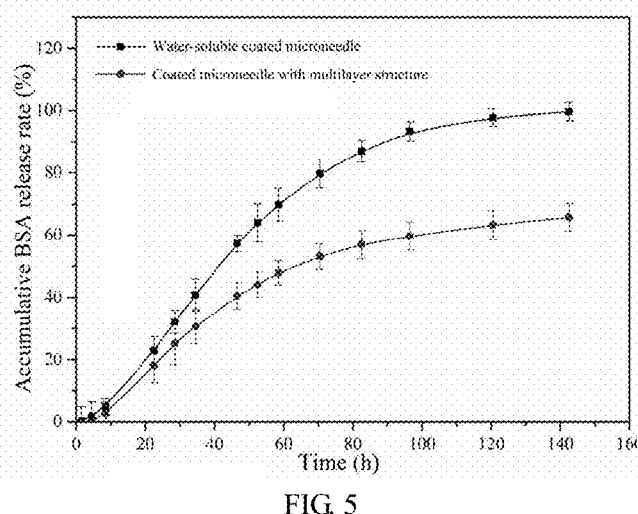
FIG. 5 illustrates a 0-140 h in-vitro release diagram of a
BSA-loaded coated microneedle prepared in example 1 of
the present application and a microneedle not added with a
crosslinked sodium alginate coating.
Figure 6:
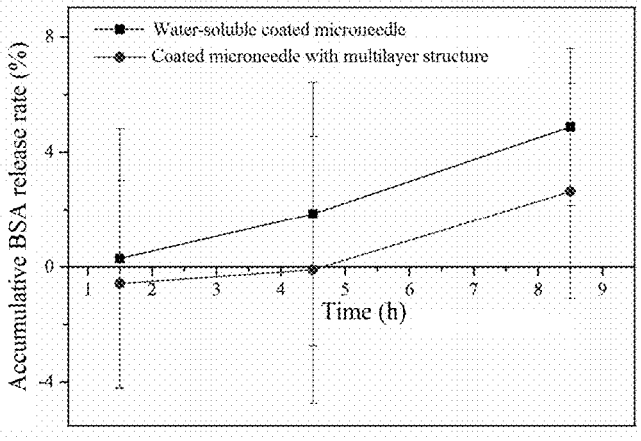
FIG. 6 illustrates a 0-9 h in-vitro release diagram of a
BSA-loaded coated microneedle prepared in example 1 of
the present application and a microneedle not added with a
crosslinked sodium alginate coating.

The prepared BSA-loaded sustained-release coated microneedle with the functional multilayer structure is as illustrated in FIG. 3. A side picture of the microneedle observed under a microscope is as illustrated in FIG. 4. The microneedle with the multilayer structure was applied to the ear skin of a newly born pig. By dissolving the BSA on the microneedle base and the surface of the pig skin, after deducting from the total drug load, it was measured that the average intake of BSA loaded by the microneedle was 94 wt %. This microneedle and the water-soluble coated microneedle were respectively placed in 500 kDa dialysis bags for in-vitro release tests to investigate the sustained-release effect of the coated microneedle with the multilayer structure. The in-vitro release diagrams of the same dose of the microneedle and the water-soluble coated microneedle are as shown in FIG. 5 and FIG. 6 (in FIG. 5 and FIG. 6, "water-soluble coated microneedle" refers to the microneedle without a crosslinked coating prepared without adding crosslinked sodium alginate; "coated microneedle with multilayer structure" refers to the coated microneedle wrapped by the swelling coating and loading BSA on the needle tip prepared in this example). From the figures, it can be clearly seen that the crosslinked swelling coating (i.e., the sustained-release layer) has delayed release and sustained release effects on the drug-loaded dissoluble coating (i.e., the content).

Example 2

Preparation of Multilayer Microneedle Patch Including Sodium Alginate Sustained-Release Layer Containing Trypan Blue 1) An appropriate amount of L-polylactic acid was placed on an integrated microneedle matrix mold. Vacuum pumping was performed at a lower position of the mold. The mold was heated at high temperature. The heating temperature was 190° C. The heating time was 5 min. A polymer material was pressed flat. Cooling and demolding were performed to obtain an integrated polylactic acid microneedle base (needle tip height was 700 μm and needle spacing was 500 μm).

2) By using water as a solvent, aqueous solution of sodium alginate with a solid content of 2% was prepared. Sodium chloride with a solid content of 0.01 mol/L was added as a pore forming agent. By using water as a solvent, 0.01 mol/L delayed crosslinking solution was prepared, which was composed of 0.01 mol/L sodium calcium edetate and 0.01 mol/L gluco-lactone. The aqueous solution of sodium alginate containing the pore forming agent and the delayed cross-linking solution were mixed according to the volume ratio v:v=10:1 to prepare solution of a crosslinked swelling material with a viscosity of 3700 cps. Uniform vortex mixing was performed for 30 s at 4000 rpm. Concentration was performed for 1 min at 5000 rpm. The solution was stood for future use.

3) The prepared solution of the crosslinked swelling material was placed in a drug loading tank with a height of 300 μm. A piece of integrated polylactic acid microneedle base was taken. The needle tip was down-wards dropped into the drug loading tank for dipping. Then, the microneedle was stood for 3 min to dry the coating.

4) By using water as a solvent and polyvinyl alcohol (33.4 cps) as a matrix, heating and swelling were performed to prepare 10% aqueous solution. Water-soluble coat-ing material solution was prepared. Trypan blue was prepared into 2% aqueous solution, which was mixed with the above coating material solution according to volume ratio v:v=1:1. Finally, dyed drug solution con-taining 5% of polyvinyl alcohol and 1% of trypan blue was formed. The viscosity of the dyed drug solution was 435 cps. Uniform vortex mixing was performed for 5 min at 2000 rpm. Centrifugation was performed for 1 min at 5000 rpm. The solution was stood for future use.

5) The prepared drug solution was placed in a drug loading tank with a height of 300 μm. The microneedle that had been loaded with the crosslinked swelling coating was taken. The needle tip was downwards dropped into the drug loading tank to dip the drug solution. Then, the microneedle was stood for 3 min to dry the coating. The solution dipping and drying pro-cess was repeated 4 times.

6) The microneedle loaded with the crosslinked swelling coating and the drug-loaded coating was dipped in the crosslinked swelling material solution again. The microneedle was stood for 3 min to dry the coating to make the exterior of the drug-loaded coating of the coated microneedle be coated with the crosslinked swelling coating.

7) A pressure-sensitive adhesive backing was bonded on the back side of the integrated base of the prepared coated microneedle to obtain a coated microneedle patch wrapped by the swelling coating and loading trypan blue on the needle tip.

Figure 7:
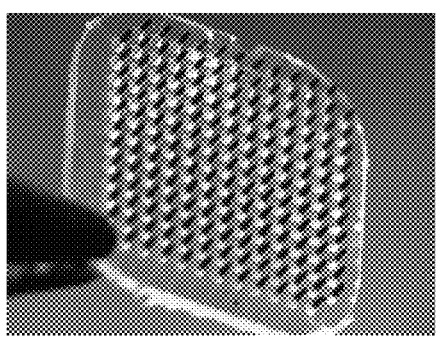
FIG. 7 illustrates a 1× stereomicroscope whole needle
shape of a Trypan-blue-loaded coated microneedle prepared
in example 2 of the present application.
Figure 8:
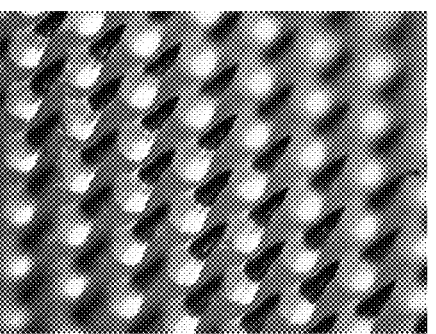
FIG. 8 illustrates a 3× stereomicroscope local needle
shape of a Trypan-blue-loaded coated microneedle prepared
in example 2 of the present application.

A 1× stereomicroscope whole needle shape of the pre-pared Trypan-blue-loaded sustained-release coated microneedle with the functional multilayer structure is as illustrated in FIG. 7, and a 3× stereomicroscope local needle shape is as illustrated in FIG. 8.

Example 3

Skin Puncture and Coating Implantation Experiment of Coated Microneedle Patch

The microneedle patch prepared in example 2 was applied to fresh pig skin, pressed with a 30N syringe for 40 s, and placed on agar hydrogel for moisturizing for 3 min. Then, the microneedle patch was removed to observe whether there was an implanted needle tip coating in the skin and whether the needle hole was clear. The removed microneedle patch was placed under a stereomicroscope to observe whether the coating on the needle tip of the inte-grated polylactic acid base had fallen off and whether there was residual dissolved trypan blue at the bottom of the base.

Figure 9:
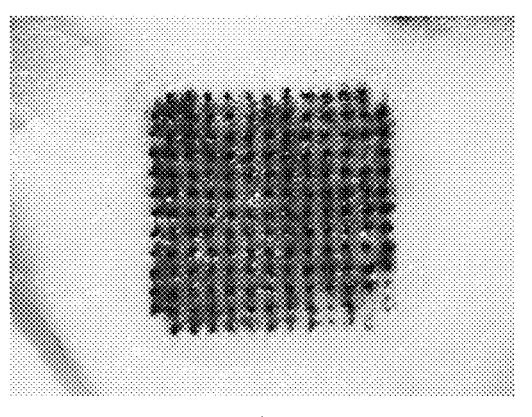
FIG. 9 illustrates effect pictures after needle tips of a
microneedle patch are implanted into a pig skin in example
3 of the present application.
Figure 9:
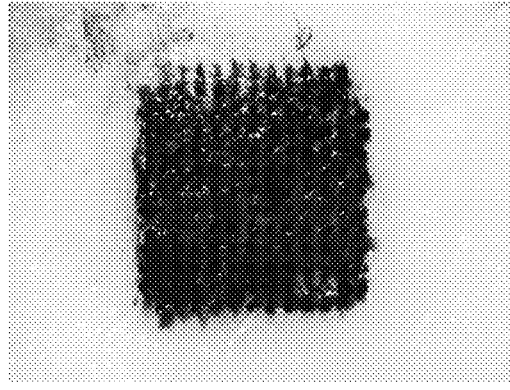
Figure 10:
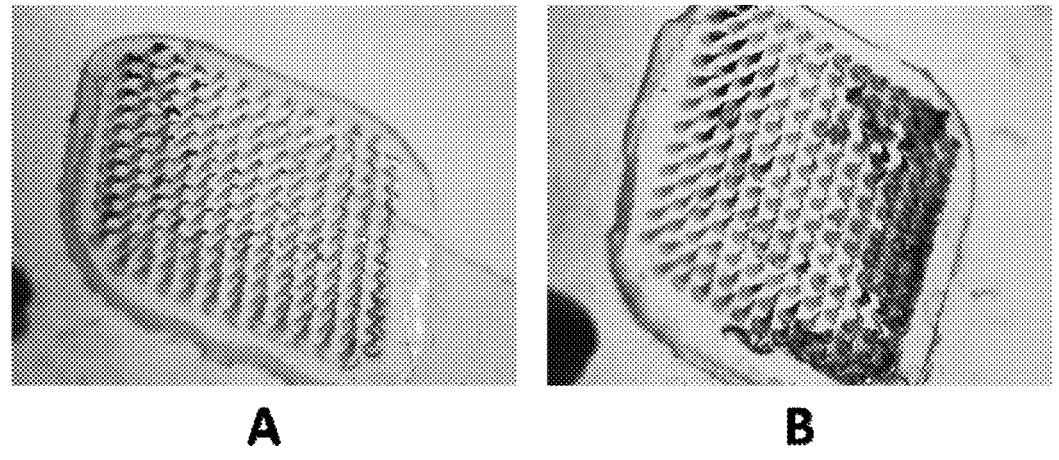
FIG. 10 illustrates dissolution pictures of a lower inte-
grated base after a microneedle patch penetrates a pig skin
in example of the present application.

FIG. 9 illustrates pictures of the pig skin after treated by microneedles. A represents the microneedle group wrapped by the crosslinked swelling coating. B represents the group without the crosslinked swelling coating. The needle hole in the pig skin in A is clearer than that in B, which indicates that the coating loading trypan blue is dissolved more slowly in the skin after being wrapped by the crosslinked coating, and simultaneously can effectively prevent the coating from overflowing from the skin, thus ensuring the intradermal drug intake. Specifically, the surface of the pig skin was gently wiped by using a cotton swab. Then, the cotton swab was soaked in normal saline for vortex oscillation for 2 h. The absorbance of the solution was measured. It was found that the drug exuded from the epidermis in A accounts for 2 wt % of the drug load of the microneedle, and the drug exuded from the epidermis in B accounts for 10 wt % of the drug load of the microneedle, indicating that the multilayer structure can ensure that the drug does not seep from the needle hole after the microneedle acts on the skin. FIG. 10 illustrates pictures of the microneedle acting on the pig skin. A represents the microneedle group wrapped by the cross-linked swelling coating. B represents the microneedle group without the crosslinked swelling coating. There is obvious trypan blue residue on the integrated base of the microneedle in B, while there is no dissolved trypan blue at the bottom of the integrated base of the microneedle in A, which indicates that when there is no delayed release effect of the crosslinked swelling coating, in the process that the dissoluble coated microneedle acts on the skin, the needle tip is dissolved quickly and the interaction between the needle tip and the skin produces resistance, which causes the needle tip coating to overflow from the skin pores, thus sticking to the bottom of the integrated base and reducing the drug intake. Specifically, the microneedle after acting on the skin was soaked in normal saline for vortex oscillation for 10 min. The absorbance of the solution was measured. It was found that the residual drug on the integrated base of the microneedle A accounts for 3 wt % of the drug load of the microneedle, and the residual drug on the integrated base of the microneedle B accounts for 24 wt % of the total drug load, indicating that the multilayer structure can guarantee the drug intake of the microneedle and improve the drug bioavailability from the perspective of drug administration. When the microneedle was subjected to in-vitro release tests, trypan blue could be released slowly for up to 15 days.

Example 4

Preparation of Multilayer Microneedle with Near-Neutral Chitosan Sustained-Release Layer Containing Recombinant Human Interferon 1) An appropriate amount of L-polylactic acid was placed on an integrated microneedle matrix mold. Vacuum pumping was performed at a lower position of the mold. The mold was heated at high temperature. The heating temperature was 190° C. The heating time was 5 min. A polymer material was pressed flat. Cooling and demolding were performed to obtain an integrated polylactic acid microneedle base (needle tip height was 700 μm and needle spacing was 500 μm).

2) By using 1% aqueous solution of lactic acid as a solvent, acidic aqueous solution of chitosan with a solid content of 1.5% was prepared. Trehalose with a solid content of 1% was added as a pore forming agent. After complete dissolution, the solution was placed in a dialysis bag with molecular cut-off of 3500 for dialysis for 3 d in ultrapure water until the pH of the chitosan solution was 6.0-6.5. The near-neutral chitosan solution was slightly heated until the solid content of the chitosan was 1.5% (confirmed by weighing). The temperature was balanced to room temperature. Centrifugation was performed for 1 min. The solution was stood for future use.

3) The prepared solution of the crosslinked swelling material was placed in a drug loading tank with a height of 300 μm. A piece of integrated polylactic acid microneedle base was taken. The needle tip was downwards dropped into the drug loading tank for dipping. Then, the microneedle was stood for 3 min to dry the coating.

4) By using water as a solvent and polyvinylpyrrolidone (K120) as a matrix, dissolution was performed in ultrapure water to prepare 5% aqueous solution. 2% of trehalose was added to prepare water-soluble coating material solution. Lyophilized powder of recombinant human interferon was prepared into 20 mg/mL aqueous solution, which was mixed with the above coating material solution according to volume ratio v:v=1:1. Finally, drug solution containing 2.5% of polyvinylpyrrolidone, 1% of trehalose and 10 mg/mL recombinant human interferon was formed. Uniform vortex mixing was performed for 5 min at 2000 rpm. Centrifugation was performed for 1 min at 5000 rpm. The solution was stood for future use.

5) The prepared drug solution was placed in a drug loading tank with a height of 300 μm. The microneedle that had been loaded with the crosslinked swelling coating was taken. The needle tip was downwards dropped into the drug loading tank to dip the drug solution. Then, the microneedle was stood for 3 min to dry the coating. The solution dipping and drying process was repeated 4 times.

6) The microneedle loaded with the crosslinked swelling coating and the drug-loaded coating was dipped in the crosslinked swelling material solution again. The microneedle was stood for 3 min to dry the coating to make the exterior of the drug-loaded coating of the coated microneedle be coated with the crosslinked swelling coating to obtain a coated microneedle wrapped by the swelling coating and loading recombinant human interferon on the needle tip.

The microneedle with the multilayer structure was applied to the ear skin of a newly born pig. By dissolving the recombinant human interferon on the microneedle base and the surface of the pig skin, after deducting from the total drug load, it was measured that the average intake of recombinant human interferon loaded by the microneedle was 97 wt %. This microneedle was placed in a 300 kDa dialysis bag for an in-vitro release test to investigate the sustained-release effect of the coated microneedle with the multilayer structure. The result shows that 90% of the drug can be slowly released within 12 d.

Example 5

Influence of Solid Content/Viscosity of Drug Solution and Drug Loading Times on Drug Load of Microneedle The preparation method is as shown in example 1 (needle tip height was 500 μm and needle spacing was 500 μm). In all formulas, in step 4), the drug solution contained 10 mg/mL BSA; in step 2), the used crosslinked swelling material solution was composed of sodium alginate solution with a total solid content of 2% and 0.3 mol/L delayed crosslinking agent, the delayed crosslinking agent was composed of 0.01 mol/L sodium edetate and 0.01 mol/L glucolactone, and the volume ratio of the sodium alginate solution to the delayed crosslinking solution was 10:1. For other corresponding parameters of the formulas, such as the PVA (6.0 cps) solid content of the drug solution and the number of times of dipping in the drug solution, see Table 1.

TABLE 1

Preparation Parameters and drug loads of formulas

| | PVA solid content in drug solution | Number of times of dripping | Drug load μg/piece |
|---|---|---|---|
| Formula 1 | 10 wt % | 1 | 0.5 |
| Formula 2 | | 2 | 0.72 |
| Formula 3 | | 3 | 1.99 |
| Formula 4 | | 4 | 5.24 |
| Formula 5 | | 5 | 8.06 |
| Formula 6 | | 6 | 10.88 |
| Formula 7 | 15 wt % | 1 | 3.94 |
| Formula 8 | | 2 | 6.6 |
| Formula 9 | | 3 | 8.78 |
| Formula 10 | | 4 | 10.66 |
| Formula 11 | | 5 | 14.82 |
| Formula 12 | | 6 | 13.75 |
| Formula 13 | 20 wt % | 1 | 3.14 |
| Formula 14 | | 2 | 7.36 |
| Formula 15 | | 3 | 10.97 |
| Formula 16 | | 4 | 13.16 |
| Formula 17 | 30 wt % | 1 | 2.18 |
| Formula 18 | | 2 | 9.37 |
| Formula 19 | | 3 | 13.59 |

As measured, the viscosity of 10 wt % PVA solution is 46.8 cps, the viscosity of 15 wt % PVA solution is 251.5 cps, the viscosity of 20 wt % PVA solution is 447.2 cps, and the viscosity of 30 wt % PVA solution is 12020 cps.

According to the drug load test, the drug load of the coated microneedle is related to the apparent viscosity of the drug solution (solid content of matrix material) and the number of times of dipping in the drug solution. Under the same drug concentration, formula 6, formula 10, formula 15 and formula 18 can reach approximately 10μ g/piece. At the same time, when dipping in the drug solution, it is observed that when the apparent viscosity of the drug solution is less than 100 cps, a capillary phenomenon occurs, and the drug load of the microneedle is too low; when the apparent viscosity of the drug solution exceeds 12000 cps, the solution is too viscous to maintain the liquid surface to be horizontal in the dipping process, which influences the drug loading uniformity. Therefore, the optimum viscosity of the drug solution is 100-12000 cps.

Figure 11:
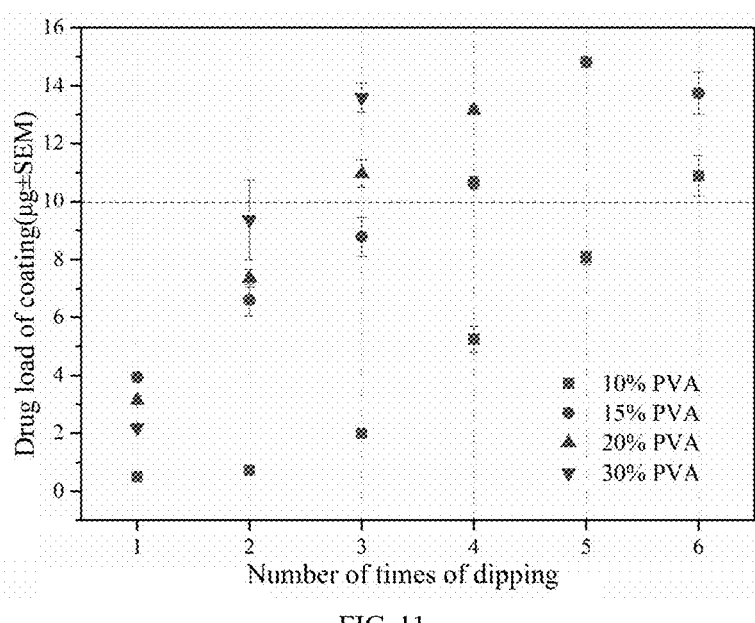
FIG. 11 illustrates a drug loading rate trend diagram of
formulas in example 5 of the present application.
Figure 12:
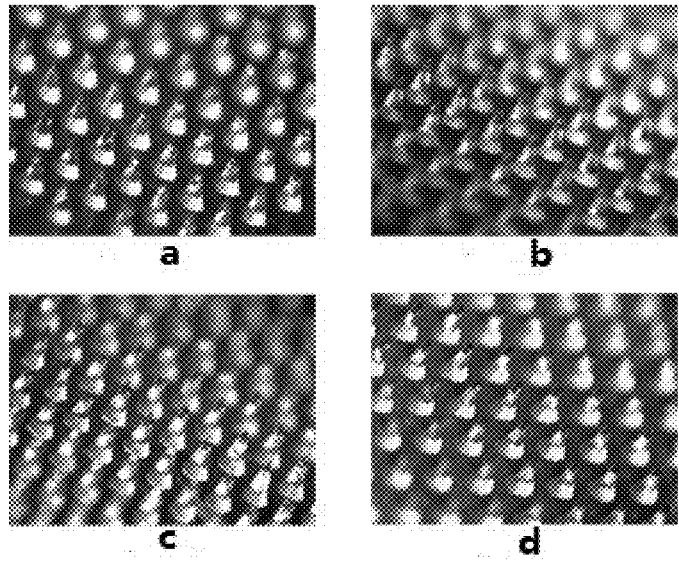
FIG. 12 illustrates 4× stereomicroscope observation pic-
tures of needle tip shapes of formulas 6/10/15/18 in example
5 of the present application.

The drug load trend of each formula in example 4 is summarized as illustrated in FIG. 11. The 4x stereomicroscope observation pictures of needle tip shapes of formulas 6/10/15/18 are as illustrated in a-d of FIG. 12 sequentially. Accordingly, it can be seen that the needle tip shapes remain intact after coating and the needle tips have the ability to puncture the skin.

Example 6

Preparation of Coated Microneedles with Different Needle Spacing, Needle Tip Heights and Coating Heights The preparation method is as shown in example 1. In all formulas, in step 4), the drug solution contained 10 mg/mL red fluorescein and 15% PVA (6.0 cps); in step 2), the used crosslinked swelling material solution was composed of sodium alginate solution with a total solid content of 2% and 0.3 mol/L delayed crosslinking agent, the delayed crosslinking agent was composed of 0.01 mol/L sodium edetate and 0.01 mol/L glucolactone, and the volume ratio of the sodium alginate solution to the delayed crosslinking solution was 10:1.

The used needle shape parameters and the drug loads of all examples are as shown in Table 2.

TABLE 2

Preparation Parameters and drug loads of comparative examples

| | Formula 20 | Formula 21 | Formula 22 | Formula 23 | Formula 24 |
|---|---|---|---|---|---|
| Needle tip height (μm) | 700 | 500 | 700 | 700 | 700 |
| Needle spacing μm) | 500 | 500 | 600 | 700 | 500 |
| Coating height (μm) | 300 | 300 | 300 | 300 | 200 |
| Number of times of loading | 3 | 3 | 3 | 3 | 3 |
| Drug load (μg/piece) | 17.41 | 5.77 | 10.94 | 6.18 | 5.75 |

Figure 13:
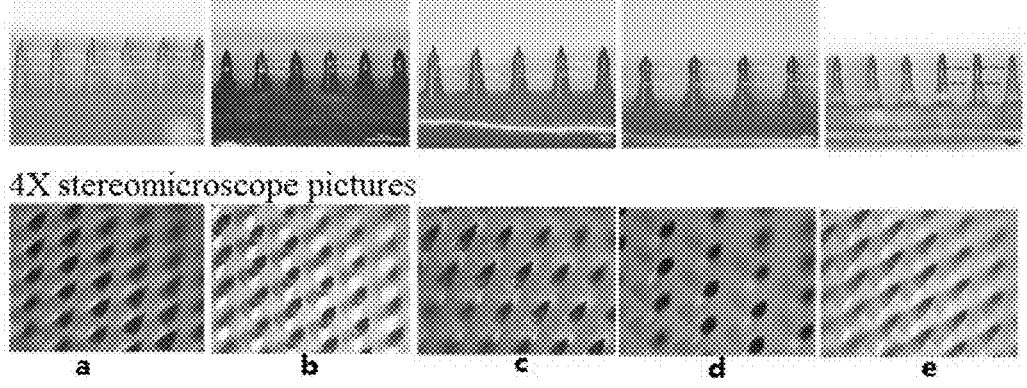
FIG. 13 illustrates 5× microscope side pictures and 4×
stereomicroscope observation pictures of formulas in
example 6 of the present application.

For the 5x microscope side pictures and 4x stereomicroscope observation pictures of formulas are as illustrated by a-e in FIG. 13 sequentially. Accordingly, it can be seen that the microneedle in the present application may have various different models and the coating thickness uniformity is good.

Examples 7-12

The preparation method is as shown in example 1. For parameters of components in examples 7-12, see Table 3.

TABLE 3

Ratio and process parameters of components

| | Example 7 | Example 8 | Example 9 | Example 10 | Example 11 | Example 12 |
|---|---|---|---|---|---|---|
| Component of integrated microneedle base | PLA | PLA | PLA | PLGA | PLGA | PCL |

TABLE 3-continued

| | | Ratio and process parameters of components | | | | |
|---|---|---|---|---|---|---|
| | Example 7 | Example 8 | Example 9 | Example 10 | Example 11 | Example 12 |
| Component of drug solution | Polyvinyl alcohol (6.0 cps) with solid content of 10% + 6 mg/mL leuprorelin + trehalose with solid content of 2% Viscosity: 6468 cps | sodium carboxymethyl cellulose (200 kDa) with solid content of 5% + 24 µg/mL recombinant human insulin + trehalose with solid content of 2% Viscosity: 5667 cps | Solid content: 5%, including hydroxypropyl methylcellulose (50.0 cps + PVPK90 (1:1) + 100 mg/mL thymopentin + sucrose with solid content of 2% Viscosity: 1300 cps | Polyvinyl alcohol (33.4 cps) with solid content of 5% + 8 mg/mL human interferon + trehalose with solid content of 2% Viscosity: 450 cps | Polyvinyl-pyrrolidone (K90) with solid content of 10% + 500 mg/mL glutathione + dextrin with solid content of 1% Viscosity is 354 cps | Sodium carboxymethyl cellulose (800 cps) with solid content of 1.47% + 120 µg/mL teriparatide acetate + glutamic acid with solid content of 2% Viscosity: 510 cps |
| Component of crosslinked swelling material solution | Sodium alginate solution with total solid content of 2% + 0.3 mol/L delayed crosslinking solution (v:v = 5:1) Viscosity: 3713 cps | Sodium alginate solution with total solid content of 0.6% + 0.1 mol/L delayed crosslinking solution (v:v = 10:1) Viscosity: 345 cps | Sodium alginate solution with total solid content of 2% + 0.2 mol/L delayed crosslinking solution (v:v = 10:1) Viscosity: 3713 cps | Sodium alginate solution with total solid content of 2% + 0.3 mol/L delayed crosslinking solution (v:v = 10:1) Viscosity: 3713 cps | Sodium alginate solution with total solid content of 2% + 0.3 mol/L delayed crosslinking solution (v:v = 5:1) Viscosity: 3713 cps | Sodium alginate solution with total solid content 0.6% + 0.1 mol/L delayed crosslinking solution (v:v = 10:1) Viscosity: 345 cps |
| Number of times of dipping in drug solution | 4 | 4 | 4 | 4 | 3 | 3 |
| Drug load | 3.5 mg/piece | 15 µg/piece | 62 mg/piece | 26 µg/piece | 230 mg/piece | 55 µg/piece |
| Skin puncture ability | Have | Have | Have | Have | Have | Have |
| In-vitro release time | Release 92% in 30 d | Release 67% in 10 d | Release 82% in 13 d | Release 83% in 7 d | Release 65% in 10 d | Release 88% in 12 d |

Examples 13-18

The preparation method is as shown in example 1. For parameters of components in examples 13-18, see Table 4.

TABLE 4

| | | Ratio and process parameters of components | | | | |
|---|---|---|---|---|---|---|
| | Example 13 | Example 14 | Example 15 | Example 16 | Example 17 | Example 18 |
| Component of integrated microneedle base | PLA | PLA | PGLA | POE | PCL | PPEs |
| Component of drug solution | Hydroxypropyl methylcellulose with solid content of 5% (12.0 cps) + 10 mg/mL azelaic acid + glycerol with solid content of | Ethyl cellulose (100 kDa) with solid content of 5% + 10 mg/mL Goserelin + Tween 40 with solid content of 2% | Sodium carboxymethyl cellulose (36.0 cps) with solid content of 5% + 8 mg/mL Finasteride + PEG400 with solid content of | Polyvinyl alcohol (6.0 cps) with solid content of 20% + 20 mg/mL amifostine + sucrose with solid content of 0.35% | Polyvinyl-pyrrolidone (K90) with solid content of 10% + 10 mg/m tranexamic acid + arginine with solid content of | carboxymethyl chitosan (60 cps) with solid content of 15% + 12 mg/mL metformin hydro-chloride + dextrin with solid |

TABLE 4-continued

| | | | Ratio and process parameters of components | | | |
|---|---|---|---|---|---|---|
| | Example 13 | Example 14 | Example 15 | Example 16 | Example 17 | Example 18 |
| | 2% Viscosity: 362 cps | Viscosity: 520 cps | 0.2% Viscosity: 331 cps | Viscosity: 447 cps | 1.5% Viscosity: 354 cps | content of 1% Viscosity: 320 cps |
| Component of crosslinked swelling | Sodium alginate solution with total solid content of 1.5% + 0.2 mol/L delayed crosslinkin g solution (v:v = 5:1) Viscosity: 420 cps | Sodium alginate solution with total solid content of 2.5% + 0.3 mol/L delayed crosslinking solution (v:v = 10:1) Viscosity: 3831 cps | Sodium alginate solution with total solid content of 2% + 0.05 mol/L delayed crosslinking solution (v:v = 10:1) Viscosity: 3713 cps | Sodium alginate solution with total solid content of 1.5% + 0.2 mol/L delayed crosslinking solution (v:v = 10:1) Viscosity: 420 cps | Sodium alginate solution with total solid content of 2% + 0.25 mol/L delayed crosslinking solution (v:v = 5:1) Viscosity: 3713 cps | Sodium alginate solution with total solid content of 2.5% + 0.3 mol/L delayed crosslinking solution (v:v = 10:1) Viscosity: 5520 cps |
| Number of times of dipping in drug solution material | 3 | 3 | 4 | 4 | 3 | 3 |
| Drug load solution | 100 µg/piece | 100 µg/piece | 147 µg/piece | 1 mg/piece | 40 µg/piece | 52 µg/piece |
| Skin puncture ability | Have | Have | Have | Have | Have | Have |
| In-vitro release time | Release 73% in 5 d | Release 68% in 7 d | Release 79% in 7 d | Release 63% in 5 d | Release 75% in 6 d | Release 84% in 13 d |

Examples 19-24

The preparation method is as shown in example 1. For parameters of components in examples 19-24, see Table 5.

TABLE 5

| | | | Ratio and process parameters of components | | | |
|---|---|---|---|---|---|---|
| | Example 19 | Example 20 | Example 21 | Example 22 | Example 23 | Example 24 |
| Component of integrated microneedl e base | PLA | PLA | PGLA | POE | PCL | PPEs |
| Component of drug solution | Sodium hyaluronate (12.0cps) with solid content of 15% + 10 mg/mL immunoglo bulin +2% wt Tween 20 Viscosity: 2253 cps | Hydroxyethyl cellulose (6.0cps) with solid content of 15% + 20 mg/mL albumin + arginine with solid content of 2% Viscosity: 283 cps | Hydroxypropyl methylcellulose (3.0  cps) with solid content of 25% + 1 mg/mL superoxide dismutase + PEG400 with solid content of 0.2% Viscosity: 261 cps | Polyvinyl alcohol (6.0  cps) with solid content of 20% + 3 mg/mL corticotropin + tyrosine with solid content of 0.1% Viscosity: 447 cps | Polyvinyl-pyrrolidone (K120) with solid content of 10% + 1 mg/mL cytochrome C + sucrose with solid content of 1.5% Viscosity: 592 cps | Deacetylat ed chitosan (10 cps) with solid content of 15% + 2 mg/mL urokinase + trehalose with solid content of 1% Viscosity: 363 cps |
| Component of crosslinked swelling material solution | Near-neutral chitosan with solid content of 2% + trehalose with solid content of 5% | Near-neutral chitosan with solid content of 5% + sucrose with solid content of 2% | Near-neutral chitosan with solid content of 2% Viscosity: 3820 cps | Near-neutral chitosan with solid content of 5% Viscosity: 5621 cps | Near-neutral chitosan with solid content of 2% + polyvinyl-pyrrolidone K90 with solid | Near-neutral chitosan with solid content of 2% + maltose with solid content of 0.1% |

TABLE 5-continued

| | Example 19 | Example 20 | Example 21 | Example 22 | Example 23 | Example 24 |
|---|---|---|---|---|---|---|
| | | | | | Ratio and process parameters of components | |
| | Viscosity: 3879 cps | Viscosity: 5621 cps | | | content of 0.1% Viscosity: 3865 cps | Viscosity: 3888 cps |
| Number of times of dipping drug solution | 3 | 3 | 4 | 4 | 3 | 3 |
| Drug load | 60 µg/piece | 100 µg/piece | 10 µg/piece | 25 µg/piece | 15 µg/piece | 5 µg/piece |
| Skin puncture ability | Have | Have | Have | Have | Have | Have |
| In-vitro release time | Release 82% in 7 d | Release 75% in 8 d | Release 80% in 10 d | Release 90% in 13 d | Release 85% in 12 d | Release 78% in 10 d |

Examples 25-26

The preparation method is as shown in example 1. For parameters of components in examples 25-26, see Table 6.

TABLE 6

| | Example 25 | Example 26 |
|---|---|---|
| | | Ratio and process parameters of components |
| Component of integrated microneedle base | PLGA | PCL |
| Component of drug solution | Hydroxypropyl methylcellulose (36.0 cps) with solid content of 5% + 2 mg/mL adenosine phosphate + Tween 20 with solid content of 2% Viscosity: 350 cps | Ethyl cellulose (100 kDa) with solid content of 5% + 1 mg/mL acyclovir + trehalose with solid content of 2% Viscosity: 1796 cps |
| Component of crosslinked swelling material solution | Sodium alginate with total solid content of 1.5% + 0.2 mol/L calcium sulfate + trehalose with solid content of 5% Viscosity: 456 cps | Sodium alginate with total solid content of 2.5% + 0.3 mol/L calcium carbonate + trehalose with solid content of 2% Viscosity: 3964 cps |
| Number of times of dipping in drug solution | 3 | 4 |
| Drug load | 20 µg/piece | 10 µg/piece |
| Skin puncture ability | Have | Have |
| In-vitro release time | Release 80% in 3 d (short sustained release time) | Release 92% in 4 d (short sustained release time) |

50

Comparative Examples 1-4

The preparation method is as shown in example 1. For parameters of components in comparative examples 1-4, see Table 7.

TABLE 7

| | Comparative example 1 | Comparative example 2 | Comparative example 3 | Comparative example 4 |
|---|---|---|---|---|
| | | | | Ratio and process parameters of components |
| Component of integrated microneedle base | PLA | PCL | PCL | POE |

TABLE 7-continued

| | Ratio and process parameters of components | | | |
| | Comparative example 1 | Comparative example 2 | Comparative example 3 | Comparative example 4 |
|---|---|---|---|---|
| Component of drug solution | Hydroxypropyl methylcellulose (36.0 cps) with solid content of 5% + 2 mg/mL triazole nucleoside+ Tween 20 with solid content of 2% Viscosity: 342 cps | Ethyl cellulose (100 kDa) with solid content of 5% + 1 mg/mL polymyocyte + trehalose with solid content of 2% Viscosity: 1796 cps | Ethyl cellulose (100 kDa) with solid content of 5% + 1 mg/mL acyclovir + trehalose with solid content of 2% Viscosity: 1796 cps | Sodium carboxymethyl cellulose (3.0 cps) with solid content 20% + 20 mg/ml arabinosyl adenine + pullulan with solid content of 0.35% Viscosity: 356 cps |
| Component of crosslinked swelling material solution | Sodium hyaluronate solution with total solid content of 1.5%+ 0.2 mol/L delayed crosslinking solution (v:v = 5:1) Viscosity: 482 cps | Chondroitin sulfate solution with total solid content of 2.5%+ 0.3 mol/L delayed crosslinking solution (v:v = 10:1) Viscosity: 556 cps | Sodium alginate with total solid content of 2.5%+ 0.3 mol/L calcium chloride Viscosity: 17000 cps | Sodium alginate solution with total solid content of 1.5% + 0.3 mol/mL EDTA + 0.3 mol/mL glucolactone (v:v = 10:1) Viscosity: 420 cps |
| Number of times of dipping in drug solution | 3 | 4 | 4 | 4 |
| Drug load | 20 μg/piece | 10 μg/piece | 10 μg/piece | 100 μg/piece |
| Skin puncture ability | Have | Have | Have | Have |
| In-vitro release time | Release 85% in 13 h (basically no sustained release effect) | Release 90% in 1 d (very short sustained release time) | Release 92% in 17 h (very short sustained release time) | Release 76% in 5 h (basically no sustained release effect) |
| Reason for no sustained release effect | Sodium hyaluronate in the sustained-release layer is not crosslinked when it meets the crosslinking solution, but is dissolved when it meets the water. | Chondroitin sulfate in the sustained-release layer is not crosslinked when it meets the crosslinking solution, but is dissolved when it meets water. | In calcium chloride are free calcium ions, sodium alginate is partially crosslinked too much, and the swelling layer is easy to fall off. | There is no Ca2+ source in the delayed crosslinked sodium alginate system of the sustained-release layer, so it is impossible to crosslink sodium alginate. |

Apparently, the above examples of the present application are only examples for clearly describing the present application, instead of limiting the implementations of the present application. For those skilled in the art, other variations or changes in different forms may be made on the basis of the above description. It is impossible to exhaust all the implementations here. All obvious variations or changes arising from the technical solution of the present application are still within the scope of protection of the present application.

The invention claimed is:

1. A coated microneedle with a multilayer structure, comprising a base, a needle tip on the base, and a functional coating, wherein the functional coating comprises a content that comprises a water-soluble polymer material and an active ingredient, and a sustained-release layer that completely wraps the content and directly contacts the needle tip, wherein the sustained-release layer comprises a first layer structure directly contacting and covering the needle tip and a second layer structure covering the content and combining with the first layer structure, whereby the content is completely wrapped between the first layer structure and the second layer structure;

wherein the sustained-release layer is a delayed cross-linked sodium alginate system, raw materials of the delayed crosslinked sodium alginate system comprising a calcium source, a glucolactone and a carrier, wherein the sustained-release layer is formed through drying and crosslinking of mixed solution formed by mixing the calcium source, the glucolactone and the carrier in water; and wherein the calcium source is in a chelating state that gradually releases Ca2+ ions upon slow decomposition of the glucolactone in water to form crosslinking with the carrier.

2. The coated microneedle with the multilayer structure according to claim 1, wherein the raw materials of the sustained-release layer further comprise a pore forming agent.

3. The coated microneedle with the multilayer structure according to claim 1, wherein the water-soluble polymer material is one or more selected from the group consisting of carboxymethyl cellulose, hydroxypropyl methyl cellulose, hydroxyethyl cellulose, carboxymethyl chitosan, chitosan and derivatives thereof, polyvinyl alcohol and derivatives thereof, polyvinylpyrrolidone and derivatives thereof, sodium hyaluronate, chondroitin sulfate, dextran and derivatives thereof, sodium alginate, poly-gamma-glutamic acid, pullulan, gelatin, polydopamine and polyacrylamide.

4. The coated microneedle with the multilayer structure according to claim 1, wherein a material for forming the base and/or needle tip comprises a biodegradable water-insoluble polymer material.

5. The coated microneedle with the multilayer structure according to claim 1, wherein the content further comprises a protective agent.

6. The coated microneedle with the multilayer structure according to claim 1, wherein the height of the functional coating is not more than ½ of the overall height of the needle tip.

7. A method for preparing the coated microneedle with the multilayer structure according to claim 1, comprising:

providing a microneedle base comprising a base and a needle tip on the base;

applying aqueous solution of one part of a material for forming the sustained-release layer to the needle tip, and performing drying to obtain a swelling layer structure A covering the needle tip;

applying aqueous solution of a material for forming the content to a surface of the layer structure A, and performing drying to obtain the content on the surface of the layer structure A; and applying aqueous solution of the other part of the material for forming the sustained-release layer to the content to cover the content and combine with the layer structure A, and performing drying to obtain a swelling layer structure B, wherein the swelling layer structure A and the swelling layer structure B jointly form the sustained-release layer, and the content is wrapped in the sustained-release layer.

8. A microneedle patch, comprising the coated microneedle with the multilayer structure according to claim 1, and a backing combined with the base of the coated microneedle.

9. The coated microneedle with the multilayer structure according to claim 1, wherein, raw materials of the delayed crosslinked sodium alginate system comprise a calcium source, a glucolactone and a carrier; wherein, the calcium source is one or more selected from the group consisting of sodium calcium edetate, calcium carbonate and calcium sulfate; and wherein, the carrier is sodium alginate.

10. The coated microneedle with the multilayer structure according to claim 9, wherein, the calcium source is sodium calcium edetate.

11. The coated microneedle with the multilayer structure according to claim 1, wherein in a case that the sustained-release layer is the delayed crosslinked sodium alginate system, the viscosity of the mixed solution is 70 cps-13000 cps; the concentration of the calcium source in the mixed solution is 3 mmol/mL-0.3 mo/mL; and the molar concentration of the glucolactone in the mixed solution is 1-2 times of the molar concentration of the calcium source; or in a case that the sustained-release layer is the near-neutral chitosan system, the sustained-release layer is a structure formed through drying and swelling of solution obtained by dissolving a chitosan material in an acidic solution and dialyzing to a near-neutral level in water with the viscosity of the solution is 70 cps-13000 cps.

12. The coated microneedle with the multilayer structure according to claim 1, wherein the pore forming agent is one or more selected from the group consisting of sodium chloride, sodium carbonate, sodium bicarbonate, ammonium bicarbonate, polyvinylpyrrolidone, hyaluronic acid and sodium salt thereof, cellulose derivatives, trehalose, maltose and cyclodextrins; and the pore forming agent accounts for 0.1-10 wt % of the total weight of the sustained-release layer.

13. The coated microneedle with the multilayer structure according to claim 1, wherein the active ingredient is one or more selected from the group consisting of water-soluble chemical drugs, polypeptide drugs, protein drugs and nucleic acid drugs; and wherein the solid content of the active ingredient does not exceed 2 times of the solid content of the water-soluble polymer material.

14. The coated microneedle with the multilayer structure according to claim 1, wherein the biodegradable water-insoluble polymer material is one or more selected from the group consisting of polyanhydrides, poly(orthoesters), polyphosphoesters, aliphatic polyesters and derivatives thereof;

wherein the polyanhydrides are one or more selected from the group consisting of P(CPP-SA), P(FA-SA) and P(FAD-SA); and wherein the aliphatic polyesters and derivatives thereof are one or more selected from the group consisting of polyglycolide, polylactide, glycolide-lactide copolymer, polycaprolactone, L-polylactic acid, racemic polylactic acid, polyethylene glycol-polylactic acid copolymer and derivatives thereof.

15. The coated microneedle with the multilayer structure according to claim 1, wherein the protective agent is one or more selected from the group consisting of polyhydroxy compounds, carbohydrate compounds, serum albumin, polyvinylpyrrolidone, chondroitin sulfate, amino acids and surfactants; and wherein the protective agent accounts for equal to or less than 50% of the total mass of the content.

16. The coated microneedle with the multilayer structure according to claim 1, wherein the height of the functional coating is not more than ³/₇; and wherein the maximum diameter of the functional coating is not more than ⅔ of the bottom diameter of the needle tip.

17. The coated microneedle with the multilayer structure according to claim 16, wherein the maximum diameter of the functional coating is not more than ½ of the bottom diameter of the needle tip.

18. A coated microneedle with a multilayer structure, comprising a base, a needle tip on the base, and a functional coating on the needle tip, wherein the functional coating comprises:

(i) a content comprising a water-soluble polymer material and an active ingredient, and (ii) a sustained-release layer that completely wraps the content and directly contacts the needle tip, wherein the sustained-release layer is formed by a process comprising:

(a) applying and drying a first portion of a sustained-release precursor solution on the needle tip to form a bottom swelling layer, wherein the sustained-release precursor solution comprises a delayed crosslinked sodium alginate system comprising a calcium source in a chelating state, a glucolactone and a carrier mixed in water, (b) applying and drying the content on the bottom swelling layer, and (c) applying and drying a second portion of the sustained-release precursor solution over the content to completely encapsulate the content within the sustained-release layer;

wherein the calcium source gradually releases Ca2+ ions upon slow decomposition of the glucolactone in water to form crosslinking with the carrier during and after drying; and wherein the sustained-release layer, after insertion into skin, swells with water and delays dissolution of the content to provide sustained release of the active ingredient over at least 24 hours.

19. A coated microneedle with a multilayer structure, comprising a base, a needle tip on the base, and a functional coating on the needle tip, wherein the functional coating comprises:

(i) a content comprising a water-soluble polymer material and an active ingredient, and (ii) a sustained-release layer that completely wraps the content and directly contacts the needle tip, wherein the sustained-release layer is formed by a process comprising:

(a) applying and drying a first portion of a near-neutral chitosan solution on the needle tip to form a bottom swelling layer, (b) applying and drying the content on the bottom swelling layer, and (c) applying and drying a second portion of the near-neutral chitosan solution over the content to completely encapsulate the content;

wherein the sustained-release layer, after insertion into skin, swells with water and delays dissolution of the content to provide sustained release of the active ingredient over at least 24 hours.

* * * * *